United States Patent
Kang et al.

(10) Patent No.: US 10,585,105 B2
(45) Date of Patent: Mar. 10, 2020

(54) METHOD FOR DIAGNOSING DISEASES THROUGH OLIGOMER ANALYSIS OF ABNORMALLY AGGREGATED PROTEINS

(71) Applicant: KOREA INSTITUTE OF SCIENCE AND TECHNOLOGY, Seoul (KR)

(72) Inventors: Ji Yoon Kang, Seoul (KR); Kyeong Sik Shin, Seoul (KR); Jae Hoon Ji, Seoul (KR); Tae Song Kim, Seoul (KR); Young Soo Kim, Seoul (KR); Sang Yun Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 144 days.

(21) Appl. No.: 15/565,503

(22) PCT Filed: May 18, 2016

(86) PCT No.: PCT/KR2016/005278
§ 371 (c)(1),
(2) Date: Oct. 10, 2017

(87) PCT Pub. No.: WO2017/119553
PCT Pub. Date: Jul. 13, 2017

(65) Prior Publication Data
US 2018/0080946 A1  Mar. 22, 2018

(30) Foreign Application Priority Data
Jan. 5, 2016 (KR) .................. 10-2016-0001018

(51) Int. Cl.
*G01N 33/53* (2006.01)
*G01N 25/18* (2006.01)
*G01N 24/00* (2006.01)
*G01N 27/00* (2006.01)
*G01N 33/68* (2006.01)
*G01N 27/02* (2006.01)

(52) U.S. Cl.
CPC ......... *G01N 33/6896* (2013.01); *G01N 27/02* (2013.01); *G01N 27/026* (2013.01); *G01N 2333/47* (2013.01); *G01N 2333/4709* (2013.01); *G01N 2800/28* (2013.01)

(58) Field of Classification Search
None
See application file for complete search history.

(56) References Cited

U.S. PATENT DOCUMENTS

2008/0299111 A1  12/2008  Delacourte
2011/0166035 A1   7/2011  Kleinschmidt et al.

FOREIGN PATENT DOCUMENTS

JP    2013-511734 A   4/2013
KR    10-0595495 B1   6/2006
KR    10-1173677 B1   8/2012

OTHER PUBLICATIONS

Kyeong-Sik Shin et al., "Highly Sensitive Detection of Amyloid Beta for Alzheimer's Disease Diagnosis Using Bead-based Impedance Spectrometry", Alzheimer's & Dementia: The Journal of the Alzheimer's Association, Poster Presentation: PI, P1-038, Jul. 2015, pp. P352, vol. 11, No. 7.

Mikko Hölttä et al., "Evaluation Amyloid-β Oligomers in Cerebrospinal Fluid as a Biomarker for Alzheimer's Disease", PloS One, 2013, inner pp. 1-8, vol. 8, No. 6.

Jo V. Rushworth et al., "A Label-free Electrical Impedimetric Biosensor for the Specific Detection of Alzheimer's Amyloid-beta Oligomers", Biosensors and Bioelectronics, 2014, pp. 83-90, vol. 56.

*Primary Examiner* — Olga N Chernyshev
(74) *Attorney, Agent, or Firm* — Rabin & Berdo, P.C.

(57) ABSTRACT

The present invention relates to a method for diagnosing a disease using an analysis of oligomer of an abnormal aggregated protein includes: (1) preparing a body fluid sample including at least one of blood, blood plasma, blood serum, saliva, urine, tear, and mucus; (2) making a dilution of the body fluid sample; (3) using a biosensor to measure and detect an aggregated protein in the diluted body fluid sample; (4) analyzing a signal change of the biosensor caused by the dilution of the aggregated protein to determine a slope according to the dilution from the measurements; and (5) analyzing a proportion of the oligomer from the slope according to the dilution to make a diagnosis. The method uses a biosensor to measure the impedance and the protein concentration of blood and detects the slope according to the numerical value of the monomer and the oligomer to diagnose normal or abnormal protein aggregation or the associated diseases with more accuracy.

5 Claims, 11 Drawing Sheets

METHOD FOR DIAGNOSING DISEASES THROUGH OLIGOMER ANALYSIS OF ABNORMALLY AGGREGATED PROTEINS

TECHNICAL FIELD

The present invention relates to an analysis method of the aggregated protein content in a body fluid. More particularly, the present invention relates to a method for diagnosing a disease using an analysis of oligomer in an abnormal aggregated protein that involves measuring a concentration change of a protein in a body fluid like blood according to a dilution ratio and detecting a slope to estimate a proportion of the monomer and oligomer of the protein and thereby to make a diagnosis of normal or abnormal protein aggregation or the associated diseases with accuracy.

BACKGROUND ART

Neuronal dysfunctions and impairments are caused by toxic aggregation-prone proteins, and they are characteristic to many neurological disorders, which include, for example, amyotrophic lateral sclerosis, Alzheimer's disease, Parkinson's disease, prion disease, polyglutamine expansion diseases, spinocerebellar ataxia, spinal/spinobulbar muscular atrophy, spongiform encephalopathy, tauopathy, Huntington's disease, dystonia, and so forth.

The proteins coding the toxic aggregation-prone proteins causing the diseases and the genes coding the proteins have been identified. The normal metabolizing enzymes recirculate the proteins participating in the permanent circulation of synthesis and decomposition. In the mutation of genes, misfolded proteins accumulate and decompose in an abnormal manner. Such misfolded proteins are known to incur the formation of inclusion bodies and plaques of neurons that may indicate a damage of the neurons. It is therefore important to understand cellular mechanisms and to identify molecular means essential in reducing, inhibiting and improving the misfolded proteins. In addition, reasonable and effective therapeutic methods for those diseases can be exploited from the understanding of the effects of protein misfolding and aggregation on the survival of neurons.

Korean Patent No. 100595495 (registered on Jun. 23, 2006) discloses a diagnosis kit of Alzheimer's patient against normal persons that uses a secondary antibody-marker conjugate and a chromogenic substrate solution for the marker to participate in the antigen-antibody reaction of a specific amyloid β.

Korean Patent No. 1173677 (registered on Jul. 7, 2012) suggests a pharmaceutical composition for preventing or treating a disease associated with amyloid β accumulation, which composition contains EPPS(N-2-hydroxyethyl)piperazine-N'-(3-propanesulfonate)) represented by a specific chemical formula as an active component.

As illustrated in the patent documents of the prior art, the conventional methods use a biosensor to detect the impedance or protein concentration of blood necessary for a diagnosis and compares the impedance or protein concentration of blood with a reference value of a normal person to diagnose normal or abnormal protein aggregation or the associated diseases.

But, the measurements (numerical values) of the protein concentration or impedance of blood are not enough to clarify the difference between a normal person and a patient, so it is impossible to tell a patient from a normal person or to make a diagnosis with accuracy. Namely, the measurements (numerical values) of the protein concentration or impedance of blood do not have a clear distinction between a normal person and a patient enough to definitely tell the patient from the normal person, resulting in reducing the accuracy and reliability of the diagnosis.

PRIOR DOCUMENTS

Patent Documents (Patent Document 1)
Korean Patent No. 100595495 (registered on Jun. 23, 2006)
(Patent Document 2)
Korean Patent No. 1173677 (registered on Jul. 7, 2012)

Disclosure of Invention

For solving the problems with the prior art, it is an object of the present invention to provide a method for diagnosing a disease using an analysis of oligomer of abnormal aggregated proteins using a biosensor based on electricity (impedance and current) and optics that involves using a biosensor to detect a slope of sensor signals obtained by making a dilution of an aggregated protein used as a bio-marker of a body fluid like blood in multiple steps and extracting a monomer proportion and an oligomer proportion of the protein to diagnose normal or abnormal protein aggregation and the associated diseases with accuracy.

To achieve the object of the present invention, there is provided a method for predicting a possibility of disease using an analysis of oligomer of an abnormal aggregated protein that includes: (1) preparing a body fluid sample including at least one of blood, blood plasma, blood serum, saliva, urine, tear, and mucus; (2) making a dilution of the body fluid sample; (3) using a biosensor to measure and detect an aggregated protein in the diluted body fluid sample; (4) analyzing a signal change of the biosensor caused by the dilution of the aggregated protein to determine a slope according to the dilution from the measurements; and (5) analyzing a proportion of the oligomer from the slope according to the dilution to make a diagnosis.

Effects of the Invention

The method of diagnosing a disease using an analysis of oligomer of an abnormal aggregated protein according to the present invention uses a electricity/optics-based biosensor to measure the concentration of an aggregated protein in a body fluid like blood and detects the relative proportions of the monomer and oligomer in terms of a slope according to the concentration change, thereby diagnosing normal or abnormal protein aggregation and the associated diseases with accuracy.

In addition, the neuronal exosome analysis method of determining the protein content using exosome extracted from the blood plasma as well as the blood plasma is additionally used to make the better distinction of the slope according to the relative proportions of the monomer and oligomer, thereby diagnosing normal or abnormal protein aggregation and the associated diseases with more accuracy and enhancing the reliability of the diagnosis.

BRIEF DESCRIPTIONS OF DRAWINGS

Figure 9:
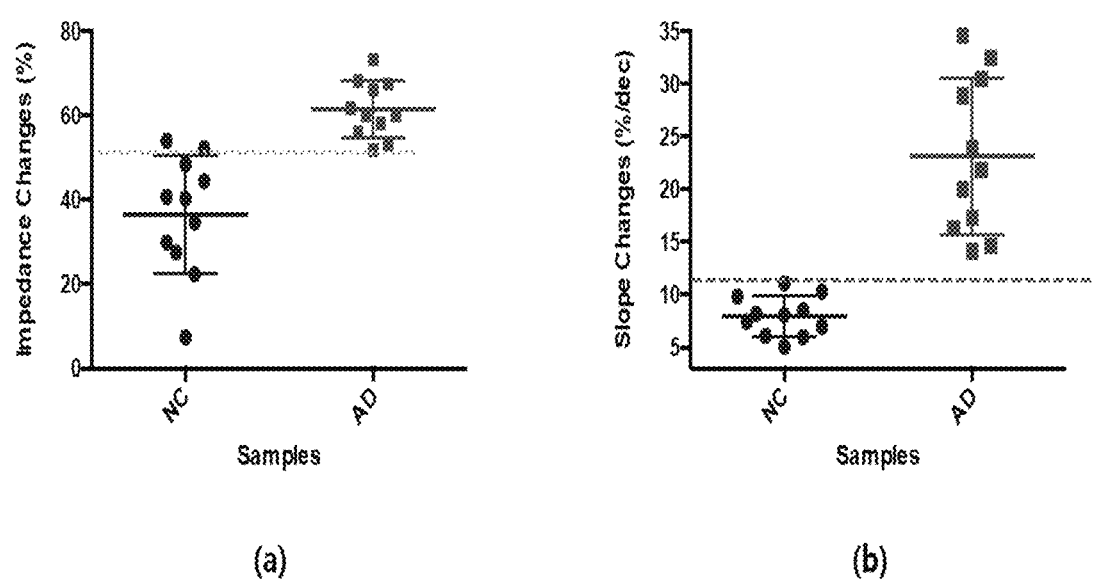

FIG. 9 presents graphs showing the impedance measurements of amyloid β extracted from neuronal exosome in blood plasma and the impedance detection results according to the slope of the impedance measurements.

Figure 10:
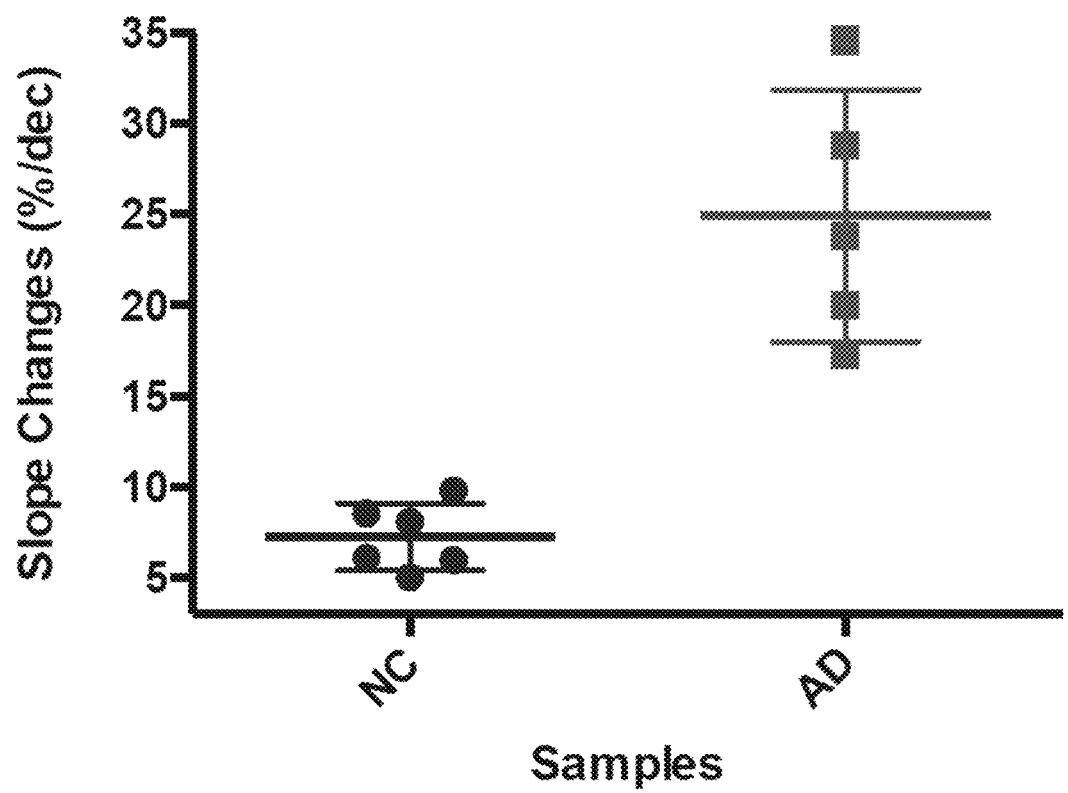

FIG. 10 is a graph showing the detection results according to the slope change of amyloid β extracted from neuronal exosome in blood plasma using an RIPA buffer.

Figure 11:
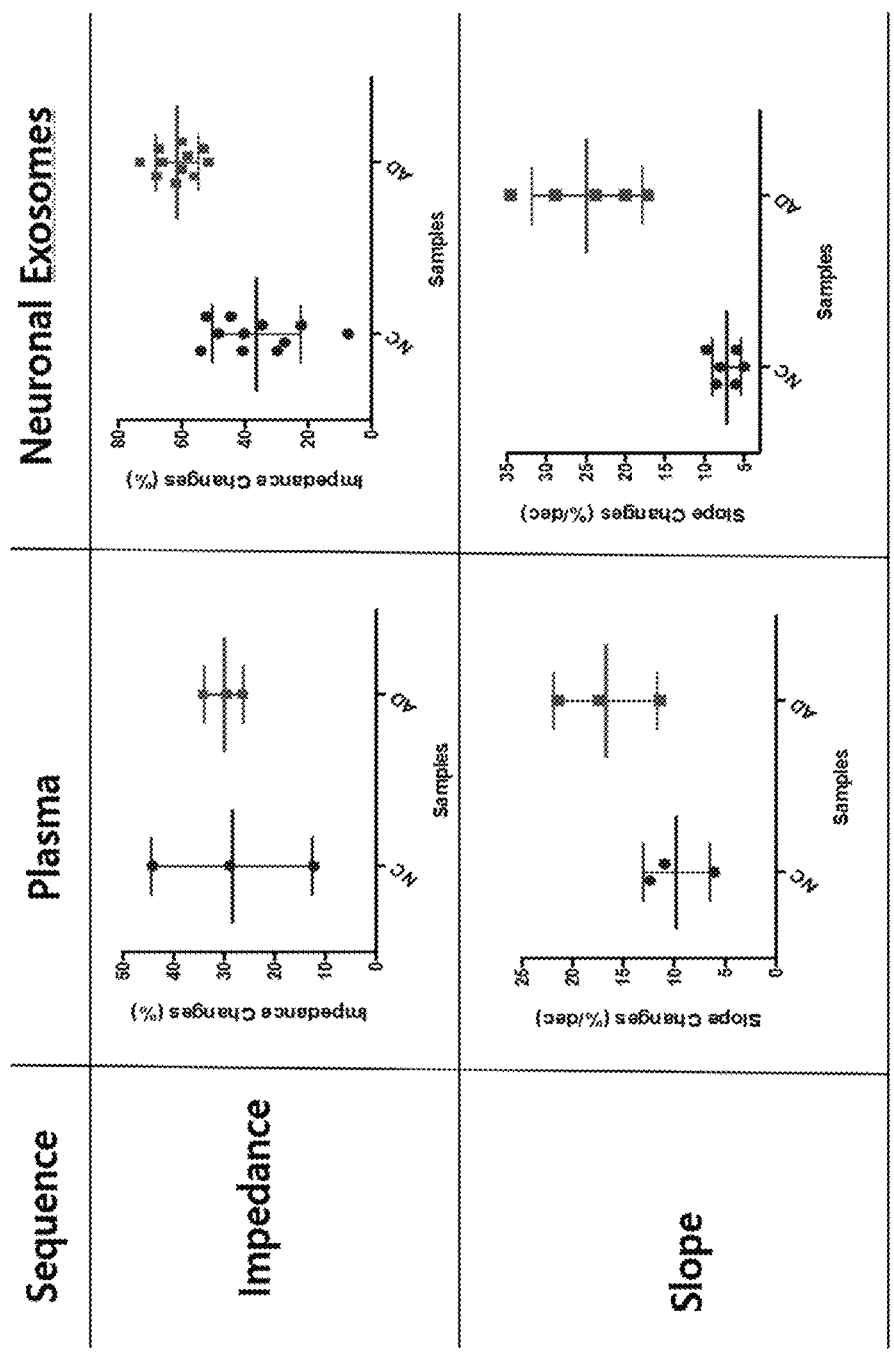

FIG. 11 presents graphs showing the detection results of impedance and slope change of amyloid β in blood plasma and the detection results of the slope change of impedance as a function of the impedance and concentration change of amyloid β extracted from neuronal exosome in blood plasma.

BEST MODES FOR CARRYING OUT THE INVENTION

Hereinafter, a detailed description will be given as to the embodiment of the present invention with reference to the accompanying drawings.

Figure 1:
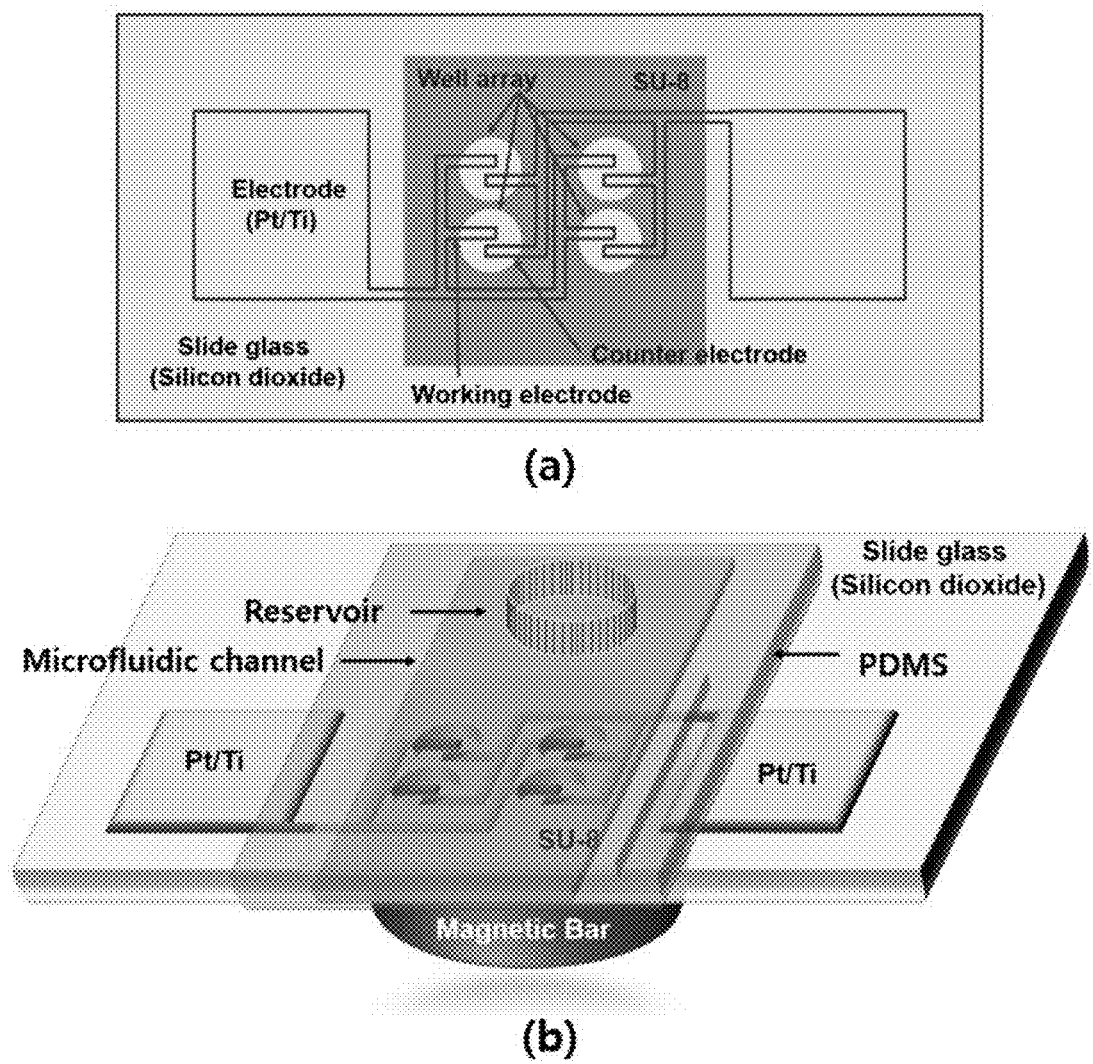
FIG. 1 is a block diagram showing the construction of an impedance biosensor used in the embodiment of the present invention.

FIG. 1 is a block diagram showing the construction of an impedance biosensor used in the embodiment of the present invention.

Referring to FIG. 1, the impedance biosensor may be comprised of an electrochemical impedance spectroscopy (EIS) sensor array (a) and a bead EIS (BEIS) platform (b). In the EIS sensor array (a), a working/counter electrode is formed of Pt/Ti metal and a microwell is made of an SU-8 electrode.

The working/counter electrode may form an array of 10*10 or 20*20 or more electrodes. Here, the microwell is to focus the electric field on the surface of magnetic beads arranged between the working/counter electrodes.

The BEIS platform (b) has a plurality of BEIS sensor arrays to form a PDMS microfluidic channel (optional), and a permanent magnet or an electromagnet arranged on the back surface of the BEIS platform (b). The size of biomolecules and the quantity of electric charge affect the output of the sensor.

Besides, the biosensor as used herein may include an optical enzyme linked immunoassay (ELISA) analytical sensor, a surface plasmon resonance (SPR) analytical sensor, and other electricity-based biosensors (e.g., FET sensors, electrochemical sensors, etc.), and so on.

Figure 2:
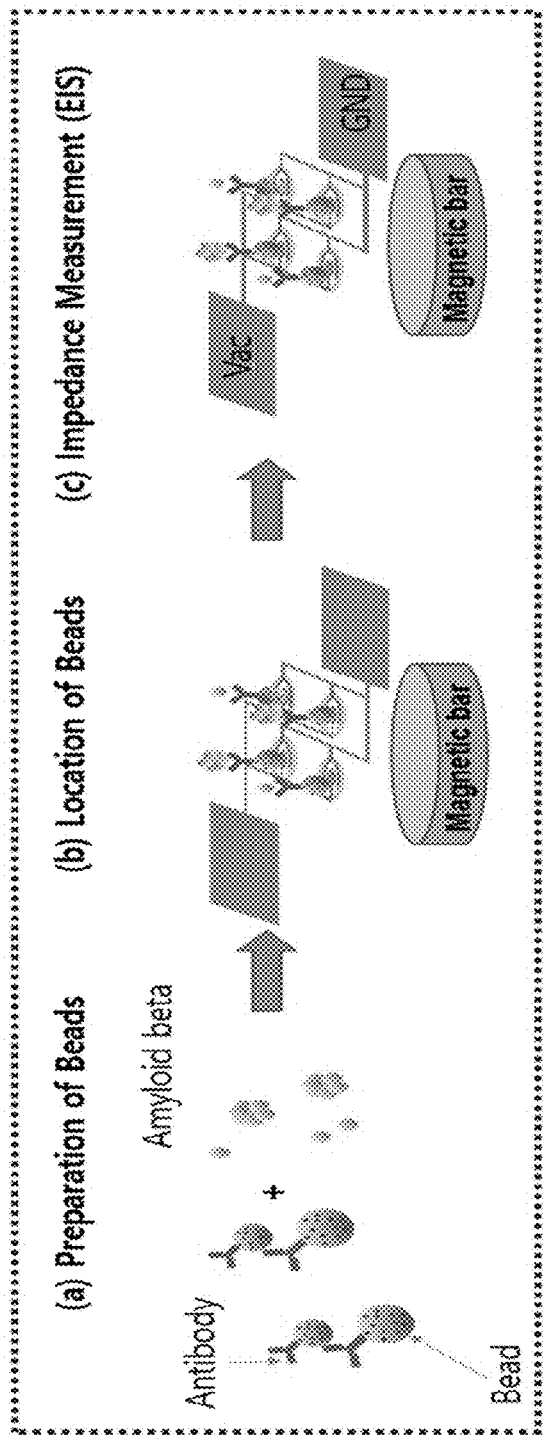
FIG. 2 is an illustration explaining a method of measuring the impedance of amyloid β using the biosensor platform of FIG. 1.
Figure 3:
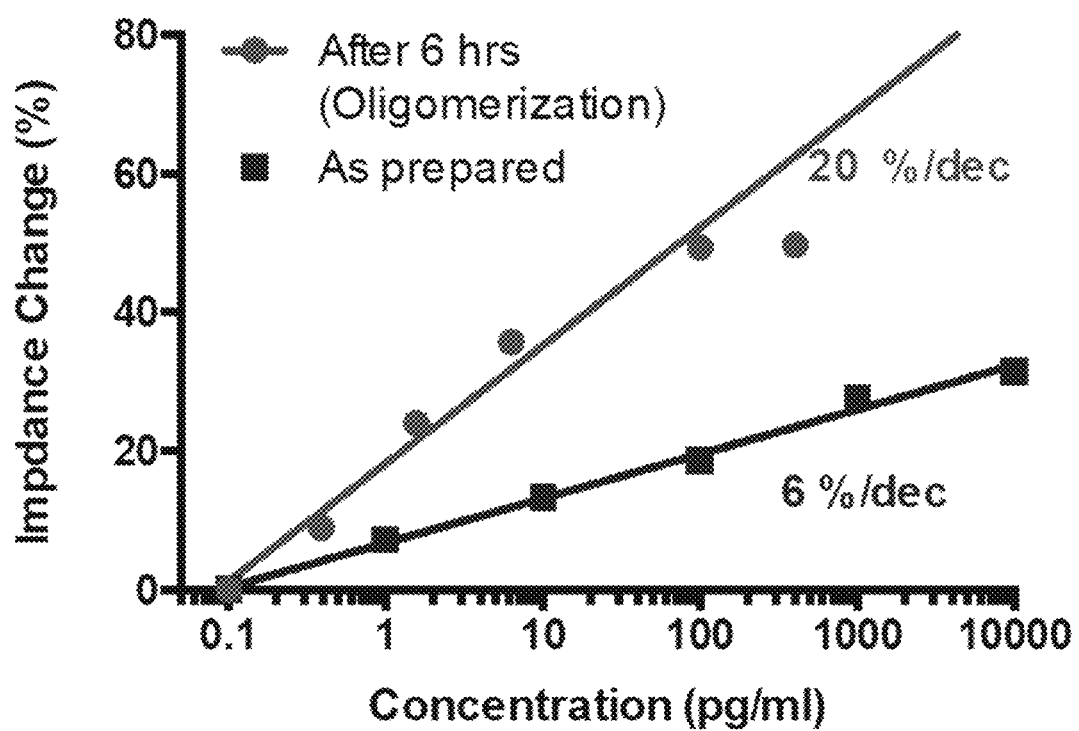
FIG. 3 is a graph showing the impedance change according to the measurement results of amyloid β of FIG. 2.

FIG. 2 is an illustration explaining a method of measuring the impedance of amyloid β using the biosensor platform of FIG. 1, and FIG. 3 is a graph showing an impedance change according to the impedance measurements of amyloid β in FIG. 2.

Reference will be made to FIG. 2 to describe a method of measuring the impedance of amyloid β. Firstly, a first antibody 1E11, amyloid β (Aβ) and magnetic beads are incubated for a predetermined time (e.g., 45 minutes) and washed with a buffer solution in order to minimize the occurrence of unspecific reactions, in step (a).

The solution containing the magnetic beads are made to flow on an electrode, which is then placed into a microwell formed on a substrate using a magnet, in step (b). A measurement is performed to detect the electrochemical impedance incurred due to the amyloid β (Aβ) participating in a reaction with the antibody and stuck to the surface of the beads. At this point, the impedance value is reduced to the relative percentage in comparison with a reference value that is the impedance value of beads not reactive to the sample. This can minimize the error by the impedance change specific to the device.

In the impedance measurement of amyloid β, the sample may be a body fluid including at least one of blood, blood plasma, blood serum, saliva, urine, tear, and mucus. The measurement may also be performed to detect the impedance of the beads reactive to at least one of Tau, alpha-synuclein, PrPsc, and Huntingtin, in addition to the impedance of the beads reactive to amyloid β.

In other words, a diagnosis is performed by measuring and graphing a change of at least one of the proportion, concentration, level, detected amount, and impedance of the monomer and the oligomer specific to a patient and a normal person, to distinguish the patient from the normal person by the oligomer-to-monomer numerical difference or the monomer-to-oligomer numerical difference. For convenience of explanation, a description will be given as to a measurement example in which a detection is made for the impedance of beads reactive to amyloid β in a prepared blood sample.

As can be seen from FIG. 3, the oligomeric amyloid β (●) has a great increase in the slope change of the electrochemical impedance. Referring to the graph, the monomeric amyloid β (■) has a different slope from the oligomeric amyloid β in the measurement of impedance change as a function of the concentration. More specifically, the slope of the monomeric amyloid β is 6%/dec, while that of the oligomeric amyloid β (Aβ) is 20%/dec. The oligomeric amyloid β (Aβ) displays the higher slope in the concentration change than the monomeric amyloid β. The impedance change is in proportion to the size of the biomolecules. When the monomeric amyloid β (Aβ) having a fixed concentration of 100 pg/ml is oligomerized, the slope in the output impedance over the concentration increases with an elapse of time. Further, the amount of the accumulating oligomeric amyloid β (Aβ) is in correspondence to the time.

Figure 4:
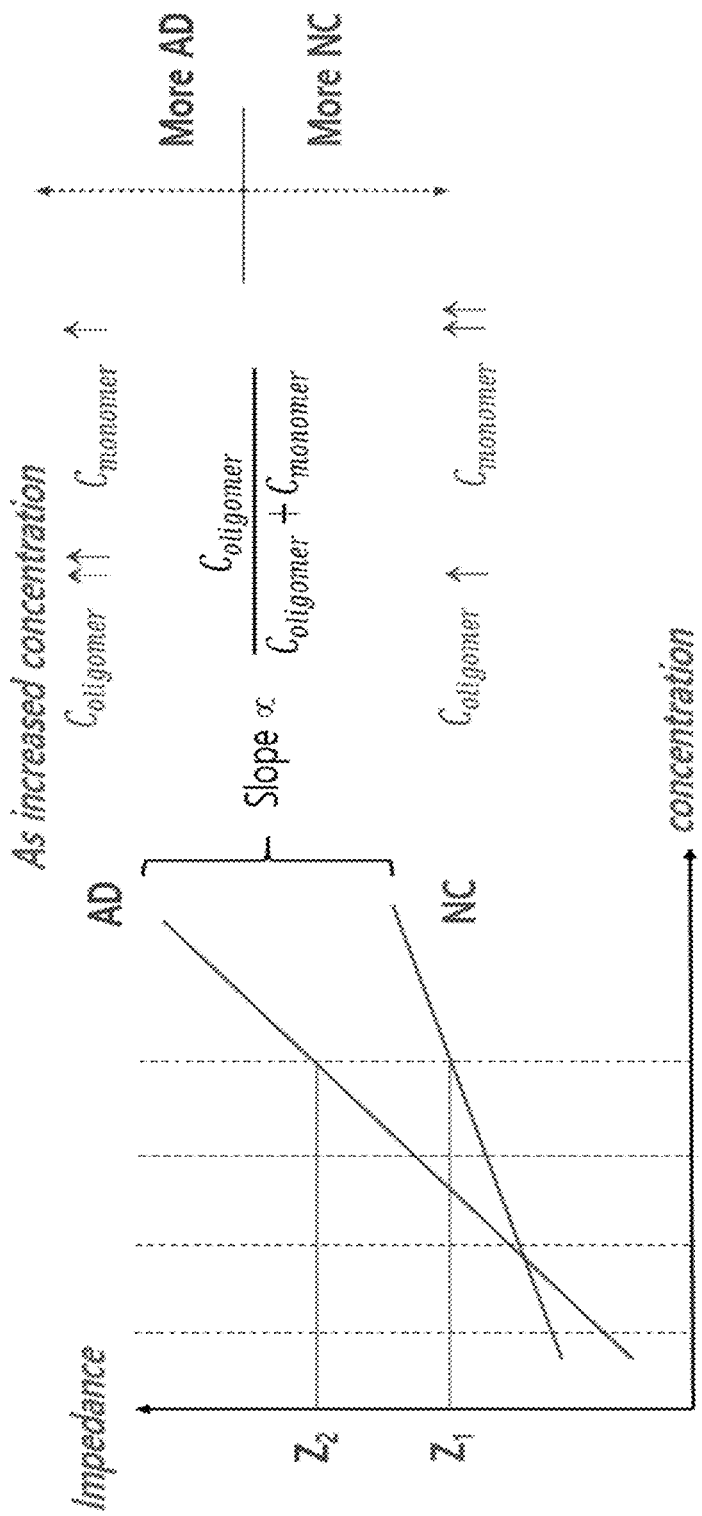
FIG. 4 is an illustration of a diagnosis method using the impedance change of amyloid β detected by the method of FIG. 2.

FIG. 4 is an illustration of a diagnosis method using the slope in the concentration change of amyloid β (Aβ) detected by the method of FIG. 2.

Referring to FIG. 4, the measurements at point Z1 and Z2 indicate the absolute amount (e.g., the total concentration) of the accumulating amyloid β (Aβ) in the body fluid samples from first and second examinees NC and AG AD, respectively. The measurements as given herein are merely experimental numerals, so the absolute amount may greatly vary depending on the physical characteristics.

Both the body fluid samples of the first and second examinees NC and AD contain a mix of monomeric amyloid β and oligomeric amyloid β. Yet, the sample of the second examinee AD has the higher content of oligomeric amyloid β. Accordingly, with an increase in the oligomeric amyloid β proportion in the sample, the second examinee has a higher slope in the concentration change.

The slope in the concentration change of amyloid β for the first or second examinee NC or AD according to the measurement at point Z1 or Z2 can be determined by the following Equation 1:

$$\text{Slope } K = \frac{\Delta y}{\log \eta} = (1 - \rho)K_m + \rho K_0 \quad \text{[Equation 1]}$$

wherein y is the signal of the sensor; ρ is the proportion of oligomer in the total amyloid β

$$\left( \rho = \frac{[A\beta_0]}{[A\beta_m] + [A\beta_0]} \right);$$

$K_m$ is the slope according to the concentration change for the monomer; $K_0$ is the slope according to the concentration change for the oligomer; and η is a dilution ratio. The concentration of the slope in the concentration change leads to the calculation of the proportion of oligomer in the total amyloid β as given by:

$$\rho = \frac{K - K_m}{K_0 - K_m}. \quad \text{[Equation 2]}$$

Namely, the numeric values of the monomer and the oligomer specific to a patient and a normal person can be expressed in terms of a slope. The diagnosis can be accomplished to distinguish the patient from the normal person by the oligomer-to-monomer numerical difference or the monomer-to-oligomer numerical difference.

Figure 5:
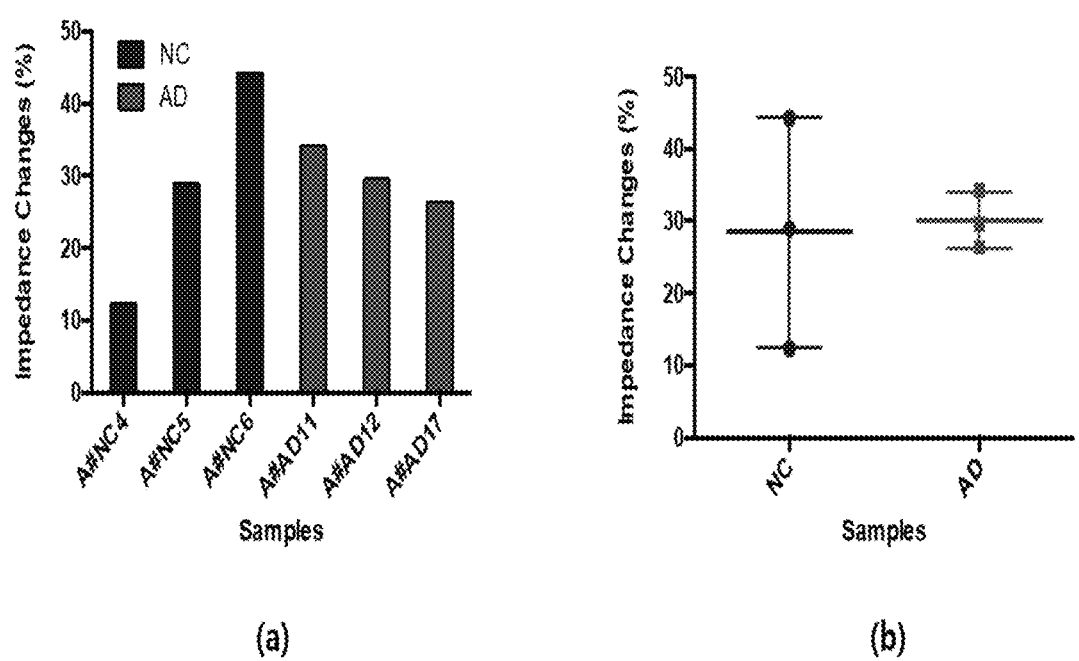
FIG. 5 is a graph showing the impedance measurements for amyloid β in blood plasma of FIG. 2.

FIG. 5 is a graph showing the impedance measurement results for amyloid β in blood plasma of FIG. 2.

As shown in FIG. 5, the electrochemical impedance measurements of the beads in the blood plasma do not provide a definite numerical distinction between the first and second examinees NC and AD. The minimum numerical difference between the first and second examinees NC and AD is the only one obtainable from the measurements. The physical differences or abilities of the first and second examinees NC and AD make the difference in the electrochemical impedance, causing the risk of misinterpretation in the diagnosis. Further, the reference value is hard to determine, which disables the definite distinction between the first and second examinees NC and AD.

Figure 6:
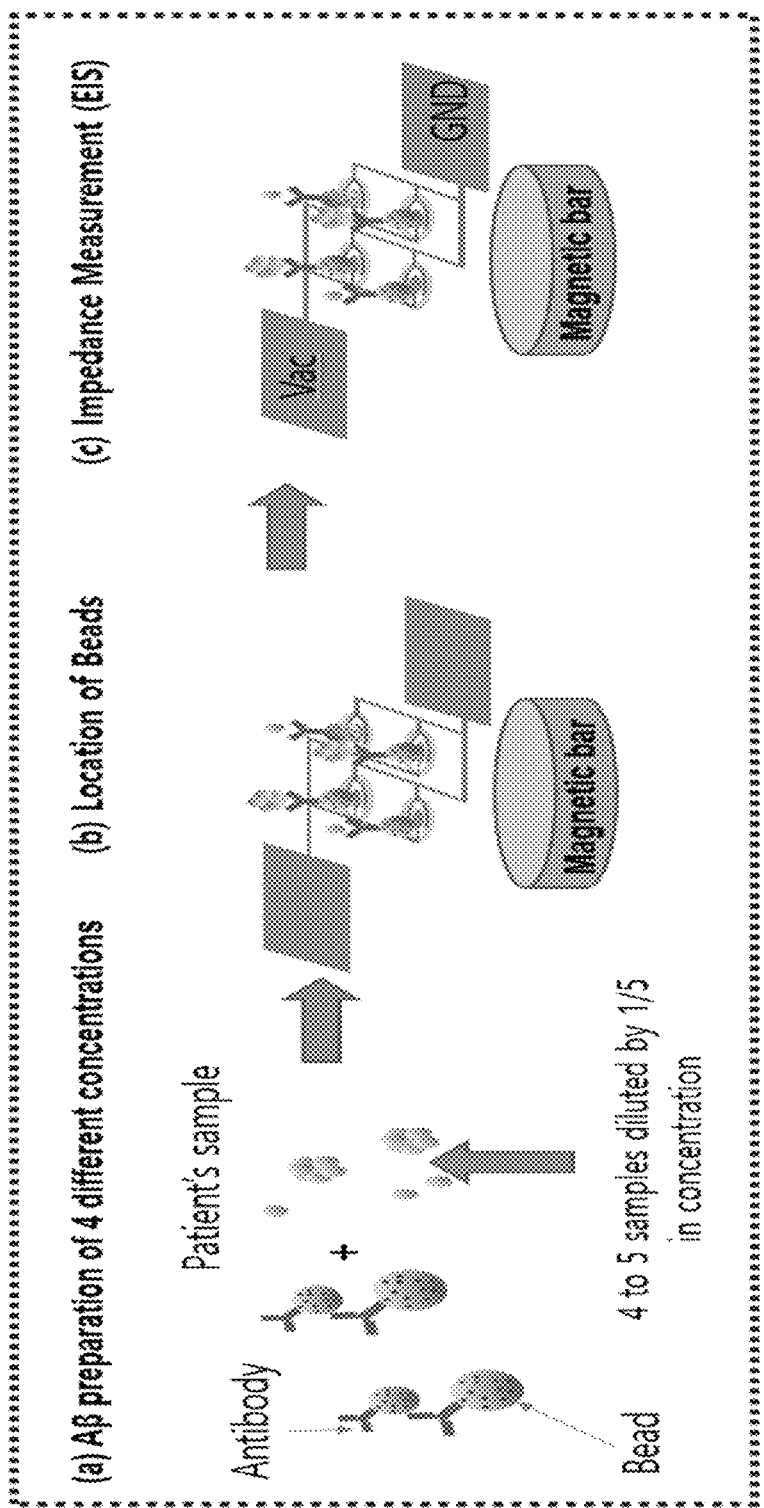
FIG. 6 is an illustration explaining a method of detecting a slope according to the concentration change of amyloid β using the biosensor platform of FIG. 1.

FIG. 6 is an illustration explaining a method of detecting a slope according to the concentration change of amyloid β using the biosensor platform of FIG. 1.

Reference will be made to FIG. 6 to describe a method of detecting the concentration of amyloid β. Firstly, antibody-bound magnetic beads is incubated for a predetermined time (e.g., 45 minutes), in step (a).

The magnetic beads with an antibody and the sample of an abnormal person (patient) in need of diagnosis are allowed to react with each other for about one hour, in step (b). At this point, the sample of the patient is diluted by ⅕ of concentration each time to prepare four to five test samples (e.g., 1, ⅕, ¹⁄₂₅, ¹⁄₁₂₅, and ¹⁄₆₂₅ in concentration), which method is desirable in the aspect of the experimental results.

Subsequently, the patient's sample beads are placed in the microwell region of an EIS sensor and measured in regards to the concentration of amyloid β, in step (c). The procedures of the steps (b) and (c) are repeated as often as the number of the patient's samples prepared in the step (a) to perform measurement and detection.

Figure 7:
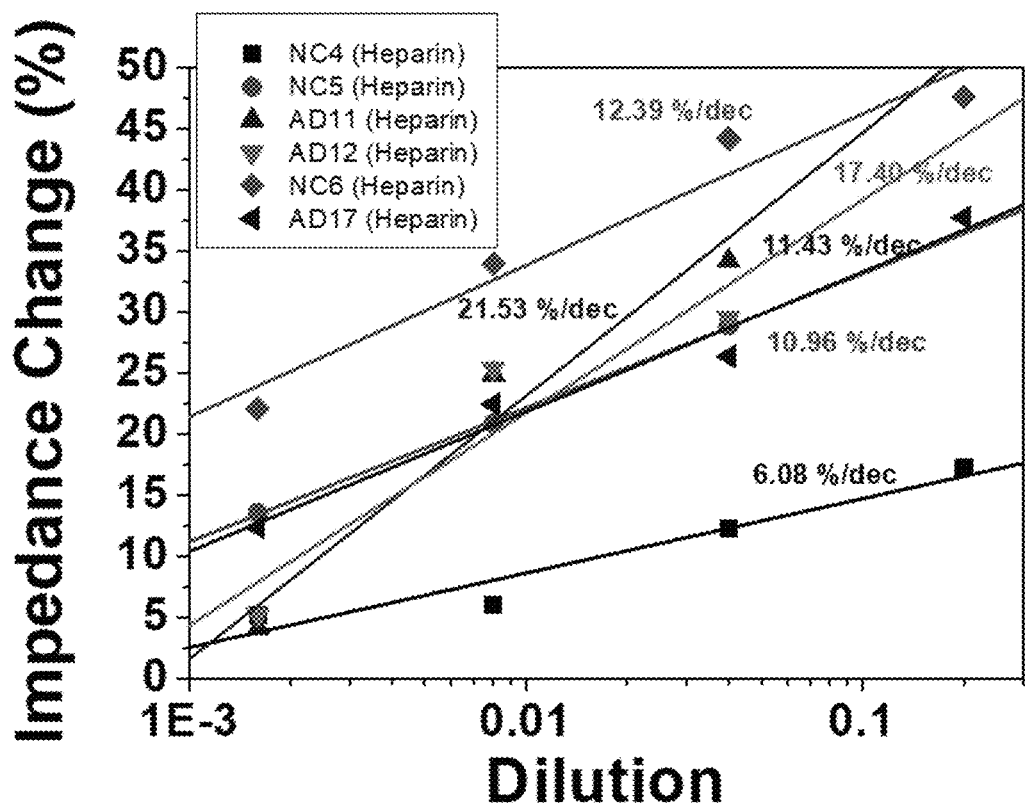
FIG. 7 is a graph showing a slope in impedance measurements according to the concentration change as a result of the detection of a slope according to the concentration change of amyloid β in FIG. 6.
Figure 8:
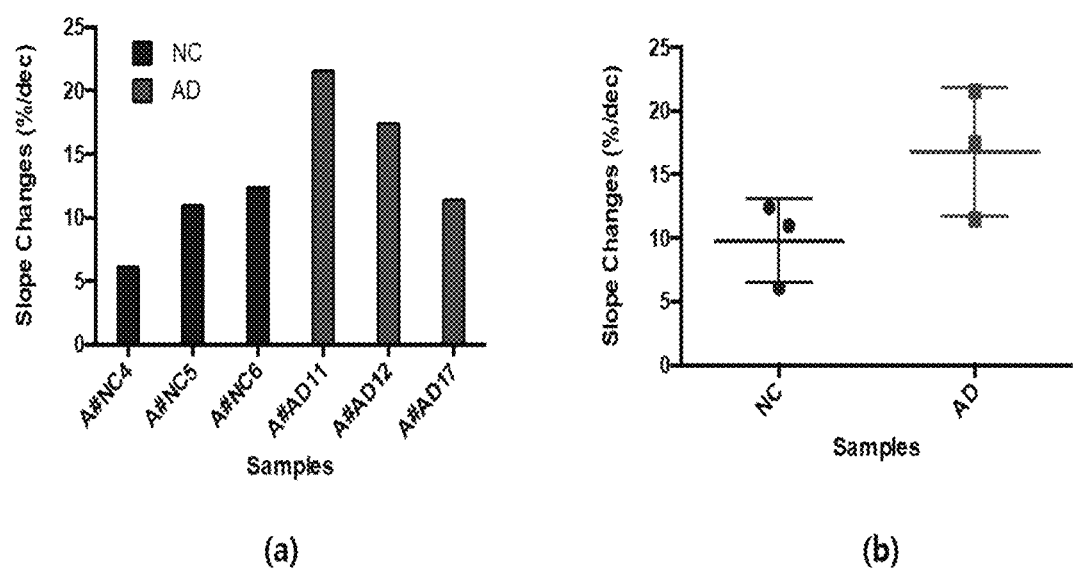
FIG. 8 is a graph showing the detection results of the concentration of amyloid β in blood plasma of FIG. 6 as a function of the slope of impedance according to the concentration change.

FIG. 7 is a graph showing a slope in impedance measurements according to the concentration change as a result of the detection of a slope according to the concentration change of amyloid β in FIG. 6. FIG. 8 is a graph showing the detection results of the concentration of amyloid β in blood plasma of FIG. 6 as a function of the slope of impedance over the concentration change.

Referring to FIGS. 7 and 8, the detection of the slope according to the concentration change of amyloid β shows a little slope difference between the whole blood samples of the first and second examinees NC and AD. The whole blood sample of the second examinee AD is separable and distinguishable to some extent, yet the existence of overlapped intervals makes it hard to distinguish the samples of the first and second examinees NC and AD. However, the slope difference can be used to distinguish the sample of the first examinee NC from that of the second examinee AD.

FIG. 9 presents graphs showing the impedance measurements of amyloid β extracted from neuronal exosome in blood plasma and the impedance change as a function of the slope change of the impedance.

As shown in FIG. 9, the beads reactive to the amyloid β in the neuronal exosome extracted from blood plasma are used to measure the impedance, and the slope change of the impedance measurements is detected. Plotting the slope change offers the clearer numerical distinction between the first and second examinees NC and AD.

Particularly, the numerical distinction for the neuronal disease is made more definite according to the neuronal exosome analysis method.

Such a distinguishing effect is attained more greatly by the method of detecting the slope according to the change of concentration, level, detected amount, and impedance of amyloid β. More specifically, the change of at least one of the numerical value, concentration, detected amount, and impedance of the monomer and the oligomer specific to a patient and a normal person is expressed in terms of a slope to distinguish the patient from the normal person by the oligomer-to-monomer numerical difference or the monomer-to-oligomer numerical difference, thereby making it possible to predict the possibility of a disease. In this regard, the threshold point is about 10% in the impedance detection method, and there may be an overlapping interval of some points. But, the method of detecting a slope change according to the change of impedance measurements can make the clearer numerical distinction between the first and second examinees NC and AD without an overlapping interval.

FIG. 10 is a graph showing the detection results as a function of the slope change of amyloid β extracted from neuronal exosome in blood plasma using an RIPA buffer.

The lysis of amyloid β using an RIPA buffer, as shown in FIG. 10, makes the clearer numerical distinction between the first and second examinees NC and AD than the neuronal exosome analysis method that includes measuring impedance of amyloid β extracted from blood plasma, detecting a slope according to the change of at least one of the numerical value, concentration, detected amount, and impedance of the monomer and the oligomer, and plotting the slope change. In other words, a graph plotting a slope according to the numerical values of the monomer and the oligomer for the first and second examinees NC and AD can provide the clearer numerical distinction between the first and second examinees NC and AD.

In both the impedance detection method and the lysis method using an RIPA buffer, the threshold point is about 13 to 14%/dec. Using an RIPA buffer offers a measurement margin of about 10% and makes the numerical distinction more clearly.

As described above, the present invention describes a method of diagnosing a disease by a relative proportion of monomer and oligomer as well as a method of analyzing a relative proportion of oligomer in proteins. In this regard, when the disease to be diagnosed by the relative proportion of monomer and oligomer is amyloidogenic disease, that is, a disease characterized by a different proportion of the monomer or the oligomer in the patient, it may be caused by aggregation of monomer into oligomer.

FIG. 11 presents graphs showing the detection results of impedance and slope change of amyloid β in blood plasma and the detection results of the slope change of impedance as a function of the impedance and concentration change of amyloid β extracted from neuronal exosome in blood plasma.

As shown in FIG. 11, the impedance measurement using amyloid β in the state of the whole blood makes the least numerical distinction between the first and second examinees NC and AD even with its numerical concentration graph.

In contrast, the impedance measurement using amyloid β extracted from the neuronal exosome of blood plasma makes the better numerical distinction between the first and second examinees NC and AD than that using amyloid β in the state of the blood plasma. Further, the use of a graph based on the slope according to the numerical values of the monomer and the oligomer makes the better numerical distinction between the first and second examinees NC and AD. In particular, a graph of the slope according to the numerical values of the monomer and the oligomer extracted from the blood plasma can be used to make the best numerical distinction between the first and second examinees NC and AD.

As described above, the method of diagnosing a disease using an analysis of oligomer of an abnormal aggregated protein includes using a biosensor to measure the impedance of blood plasma and detecting a slope according to the numerical value of the monomer and the oligomer to diagnose normal or abnormal protein aggregation and the associated diseases with more accuracy.

In addition, the neuronal exosome analysis method using an exosome in blood plasma as well as the blood plasma to determine the protein content is additionally used to make the better distinction of the slope according to the numerical values of the monomer and the oligomer, thereby diagnosing normal or abnormal protein aggregation and the associated diseases with more accuracy and enhancing the reliability of the diagnosis.

Although the exemplary embodiments of the present invention have been described, it is understood that various changes and modifications can be made by one ordinary skilled in the art within the spirit and scope of the present invention as hereinafter claimed.

What is claimed is:

1. A method of determining a ratio of oligomeric to monomeric forms of amyloid β in a body fluid sample, the method comprising:
    (1) preparing a body fluid sample;
    (2) making one or more predetermined dilutions of the body fluid sample;
    (3) measuring aggregated amyloid β protein in the diluted body fluid samples, the measuring comprising:
        providing magnetic beads having an amyloid β antibody immobilized thereon; and
        measuring an electrochemical impedance of the magnetic beads incurred due to a reaction of amyloid β with the amyloid β antibody using an electrochemical impedance spectroscopy (EIS) sensor;
    (4) analyzing a percentage change in the measured electrochemical impedance of each of the diluted body fluid samples, and determining a slope of a line based on a dilution ratio of the each of the diluted body fluid samples; and
    (5) determining the ratio of oligomeric to monomeric forms of amyloid β in the body fluid sample based on said slope of the line.

2. The method as claimed in claim 1, wherein the body fluid sample comprises one or more of exosomes, neuronal exosomes and lysed exosomes.

3. The method as claimed in claim 1, wherein the step of determining the slope of the line and the step of determining the ratio of oligomeric to monomeric forms of amyloid β in the body fluid sample based on said slope of the line comprise using the following Equations 1 and 2:

$$\text{Slope } K = \frac{\Delta y}{\log \eta} = (1-\rho)K_m + \rho K_0 \qquad [\text{Equation 1}]$$

wherein y is the signal of the sensor; p is the proportion of oligomer in the total amyloid β

$$\left( \rho = \frac{[A\beta_O]}{[A\beta_m] + [A\beta_O]} \right);$$

$K_m$ is the slope according to the concentration change for the monomer; $K_0$ is the slope according to the concentration change for the oligomer; and n is a dilution ratio, $$\rho = \frac{K - K_m}{K_0 - K_m}. \qquad [\text{Equation 2}]$$

4. The method as claimed in claim 1, wherein the amyloid β antibody is 1E11.

5. The method as claimed in claim 1, wherein the body fluid sample comprises neuronal exosomes extracted from blood plasma with radioimmunoprecipitation assay (RIPA) buffer.

* * * * *